United States Patent [19]
Chu et al.

[11] Patent Number: 6,019,879
[45] Date of Patent: Feb. 1, 2000

[54] ELECTROCHEMICAL GAS SENSOR

[75] Inventors: Edmond Y. Chu, San Diego; Chang Dong Feng, Long Beach; Richard Craig Brandt Bemis, Fullerton, all of Calif.

[73] Assignee: Teledyne Industries, Inc., Los Angeles, Calif.

[21] Appl. No.: 09/044,736

[22] Filed: Mar. 19, 1998

[51] Int. Cl.$^7$ .................................................. G01N 27/26
[52] U.S. Cl. ...................... 204/406; 204/408; 204/415; 205/783; 702/104
[58] Field of Search ................... 204/406, 408, 204/415; 324/464; 702/104, 107, 109; 205/783

[56] References Cited

U.S. PATENT DOCUMENTS

| | | |
|---|---|---|
| 4,222,006 | 9/1980 | Schneider ................................. 324/441 |
| 5,083,304 | 1/1992 | Cahill . |
| 5,166,892 | 11/1992 | Inoue et al. . |
| 5,276,615 | 1/1994 | Tournier Edmond et al. . |
| 5,642,722 | 7/1997 | Schumacher et al. . |
| 5,764,067 | 6/1998 | Rastegar ................................... 324/725 |

*Primary Examiner*—Robert J. Warden, Sr.
*Assistant Examiner*—Jennifer C. McNeil
*Attorney, Agent, or Firm*—Robert J. Pugh; Patrick Viccaro

[57] ABSTRACT

The present invention is directed to an electrochemical gas sensor network. The network includes a gas sensor for receiving a gas and for generating a target gas concentration signal. The gas sensor has an output terminal for providing an output signal that is a product of the target gas concentration signal and a first transfer function. The network also includes a compensation circuit having an input terminal connected to the output terminal of the gas sensor. The compensation circuit also has an output terminal which provides an output signal that is a product of the output signal from the gas sensor and a second transfer function. The second transfer function is approximately an inverse of the first transfer function. The present invention also contemplates a method of compensating for the attenuation of a high frequency component of an output signal of a gas sensor.

17 Claims, 4 Drawing Sheets

*RELEVANT ART*

*RELEVANT ART*

*RELEVANT ART*

*RELEVANT ART*

ELECTROCHEMICAL GAS SENSOR

CROSS-REFERENCE TO RELATED APPLICATIONS (Not Applicable)

STATEMENT REGARDING FEDERALLY SPONSORED RESEARCH (Not Applicable)

BACKGROUND OF THE INVENTION

1. Field of the Invention

The present invention is directed generally to an electrochemical gas sensor and, more particularly, to an electrochemical gas sensor with a compensated output.

2. Description of the Background

Electrochemical gas sensors are typically included in monitoring equipment to measure gas concentrations such as, for example, oxygen in a sample gas. The sensors typically display a numerical reading of the gas concentration and provide an output waveform corresponding to the gas concentration.

FIG. 5 illustrates a typical electrochemical gas sensor 10 of the relevant art. The sensor 10 includes a sensor body 12 which contains the components of the sensor 10. A cathode 14 can be constructed of, for example, a noble metal such as silver. An anode 16 can be constructed of, for example, lead. An electrolyte 18 such as, for example, an aqueous solution of potassium hydroxide, fills the sensor body 12. An expansion membrane 20 allows for expansion and contraction of the electrolyte 18 without damaging the sensor 10. A sensing membrane 22 contains the electrolyte 18 and limits the gas to be measured from having free access to the cathode 14, thus forming a diffusion barrier. The sensing membrane is constructed of, for example, Teflon®, a product of DuPont.

The electrochemical processes governing most electrochemical sensors can respond to changes in gas concentrations rapidly at times on the order of milliseconds. However, many electrochemical sensors contain diffusion barriers such as the membrane 22. These sensors are unsuitable for monitoring rapid changes in gas concentrations because the diffusion barriers, dead volume, and other factors raise their response time to changes in gas concentrations to the order of seconds. The sensors generally suffer from predictable, repeatable, and gradual reduction in sensor output with an increase in the frequency of gas concentration fluctuations. Thus, there is a need for an electrochemical gas sensor which has a rapid output response time to rapid fluctuations in gas concentrations and that compensates for the natural degradation in frequency response.

SUMMARY OF THE INVENTION

The present invention, according to its broadest implementation, is directed to an electrochemical gas sensor network. The network includes a gas sensor which receives a gas and generates a target gas concentration signal. The gas sensor has an output terminal for providing an output signal that is a product of the target gas concentration signal and a first transfer function. The network also includes a compensation circuit having an input terminal connected to the output terminal of the gas sensor. The compensation circuit also has an output terminal providing an output signal that is a product of the output signal from the gas sensor and a second transfer function which is approximately an inverse of the first transfer function.

The present invention also contemplates a method of compensating for the attenuation of a high frequency component of an output signal of a gas sensor that has a transfer function. The method includes the step of amplifying the high frequency component of the output signal with a circuit having a transfer function approximately equal to the inverse of the transfer function of the gas sensor.

The present invention represents a substantial advance over prior electrochemical gas sensors. The present invention has the advantage that it can respond to rapid changes in input gas concentrations. The present invention also has the advantage that it can compensate for the high frequency attenuation of the output of an electrochemical gas sensor due to dead volume and the presence of diffusion barriers. Those, and other advantages and benefits of the present invention, will become apparent from the Detailed Description of the Invention hereinbelow.

BRIEF DESCRIPTION OF THE DRAWING

For the present invention to be clearly understood and readily practiced, the present invention will be described in conjunction with the following figures, wherein:

FIG. 1A is a diagram illustrating a model of an electrochemical gas sensor network according to another embodiment of the present invention.

DETAILED DESCRIPTION OF THE INVENTION

It is to be understood that the figures and descriptions of the present invention have been simplified to illustrate elements that are relevant for a clear understanding of the present invention, while eliminating, for purposes of clarity, many other elements found in a typical electrochemical gas sensor. Those of ordinary skill in the art will recognize that other elements are desirable and/or required to implement an electrochemical gas sensor incorporating the present invention. However, because such elements are well known in the art, and because they do not facilitate a better understanding of the present invention, a discussion of such elements is not provided herein.

Figure 5:
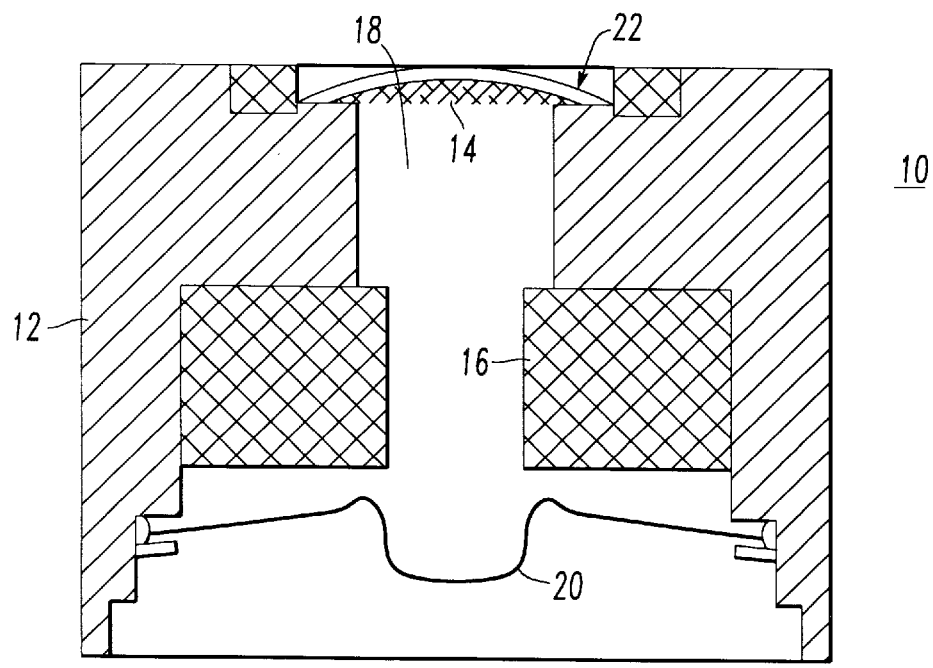
FIG. 5 illustrates a typical electrochemical gas sensor of the relevant art.

The operation of an electrochemical gas sensor, such as the sensor 10 of FIG. 5, is described hereinbelow as being designed to measure the concentration of oxygen. In the presence of oxygen, the sensor 10 creates a current that flows from the cathode 14 to the anode 16 as a result of the following electrochemical reactions:

Cathode: $O_2 + 2H_2O + 4e^- \rightarrow 4OH^-$ (1)

Anode: $2Pb \rightarrow 2Pb^{2+} + 4e^-$ (2)

Under steady state conditions, the oxygen flux reaching the cathode 14, $J_{oxygen}$, is determined by Fick's first law:

$$J_{oxygen} = -D\frac{\Delta C}{\Delta x} \quad (3)$$

where $$\frac{\Delta C}{\Delta x}$$

is the oxygen concentration gradient across the sensing membrane 22 and D is the diffusion coefficient of oxygen through the membrane 22. Typically, the diffusion coefficients of most sensing membrane materials are so low that all oxygen reaching the cathode is consumed immediately. Consequently, the oxygen concentration inside the sensor is essentially zero. Thus, the oxygen flux reaching the cathode can be expressed as:

$$J_{oxygen} = D\frac{P_{oxygen}}{d} \quad (4)$$

where $P_{oxygen}$ is the oxygen partial pressure in the sample gas and d is the sensing membrane thickness. The sensor output corresponding to a steady state situation can be expressed as:

$$I_{out} = 4FAJ_{oxygen} = 4FAD\frac{P_{oxygen}}{d} \quad (5)$$

where F is the Faraday constant, and A is the area of effective sensing membrane.

This ensures that the flux of oxygen reaching the cathode is proportional to the oxygen concentration in the sample gas.

Figure 6A:
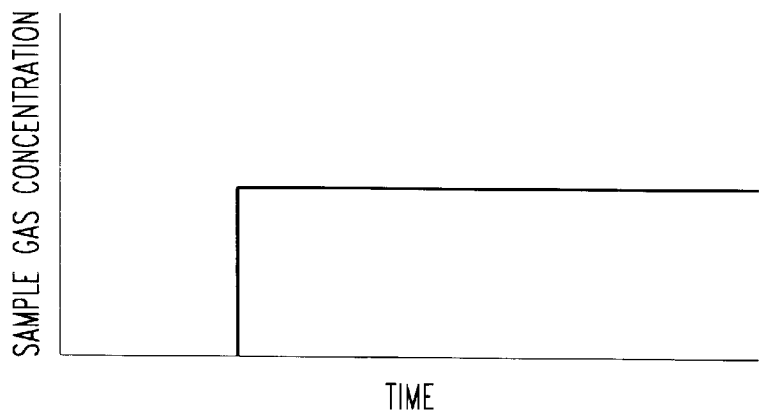
FIG. 6A illustrates a typical step change oxygen input.
Figure 6B:
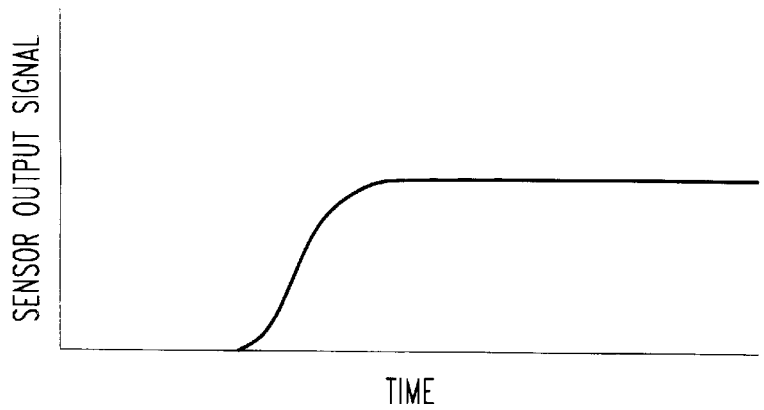
FIG. 6B illustrates the response of a typical filter of the relevant art in response to the step change of FIG. 6A.

The diffusion barrier of the sensor 10 limits the capability of the sensor 10 to monitor rapid changes in gas concentrations. FIG. 6B illustrates the response of a typical filter to the step change in gas concentration illustrated in FIG. 6A.

The time response of the sensor 10 can be obtained by solving Fick's second law:

$$\frac{\partial C}{\partial t} = D\frac{\partial^2 C}{\partial x^2} \quad (6)$$

Figure 7:
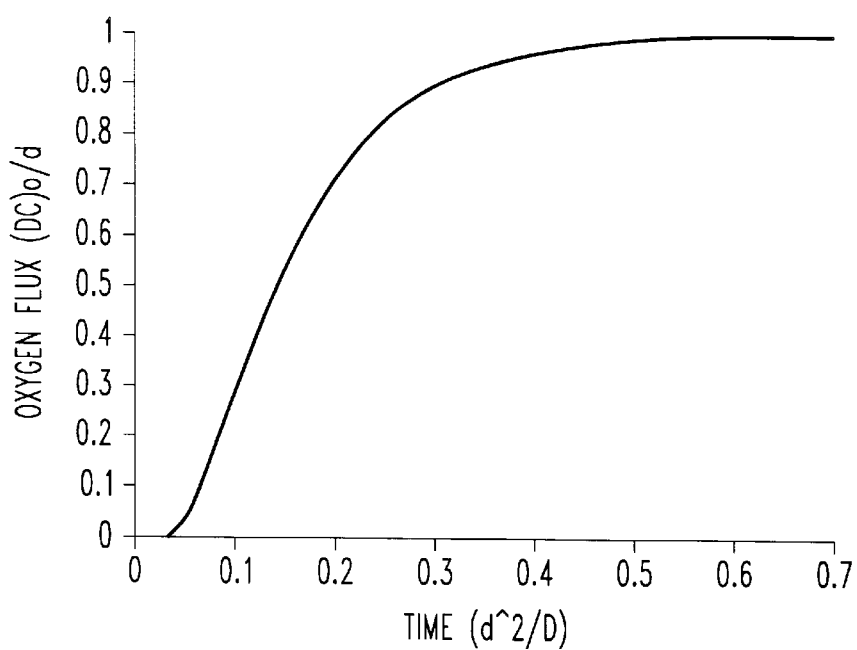
FIG. 7 illustrates the relationship between oxygen flux and time in normalized units for a typical filter.

For a step change in gas concentration, the oxygen flux reaching the cathode 14 can be expressed as:

$$J(d,t) = -D\frac{\partial C}{\partial x} = \frac{DC_0}{d}\left\{1 + \sum_{n=1}^{\infty} 2(-1)^n e^{-\frac{n^2\pi^2 Dt}{d^2}}\right\} \quad (7)$$

where $C_0$ is the oxygen concentration external to the sensor, and d is the thickness of the sensing membrane 22. FIG. 7 illustrates a plot of the oxygen flux reaching the cathode 14 versus time in normalized units, which shows a significant deviation from a step function. The expression of J(d,t) indicates that the sensor still has a large number of time-varying components corresponding to the higher order terms of the expression.

An electrochemical gas sensor, such as the sensor 10 of FIG. 5, can be modeled electrically as an ideal sensor (one that has unlimited high frequency response) connected in series with a low pass filter network that matches the high frequency attenuation of the sensor 10.

The ideal sensor has a flat frequency response. Thus, its output amplitude for a sinusoidal input gas concentration would be the same for any frequency of input oxygen concentration. However, the low pass filter network attenuates the high frequency components of the ideal sensor output.

Figure 1:
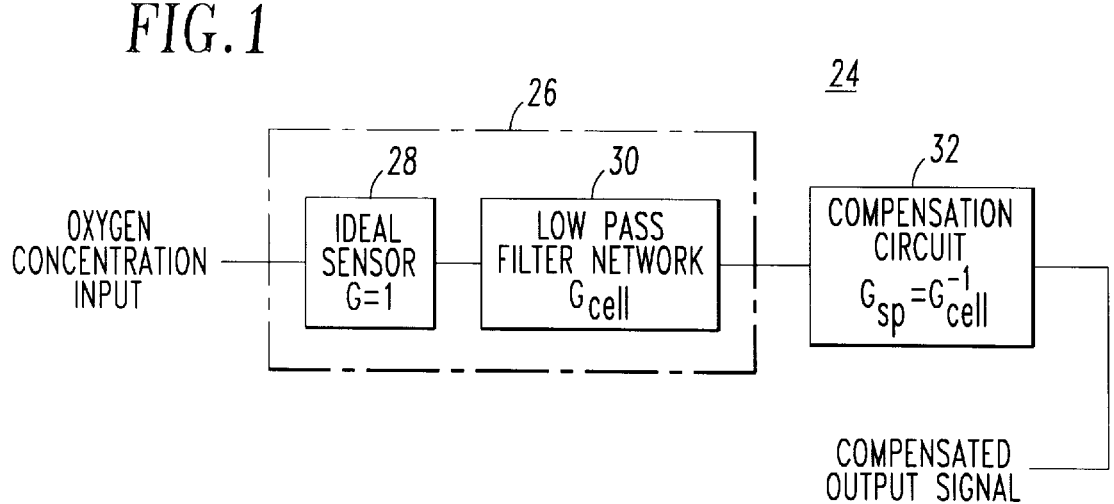
FIG. 1 is a diagram illustrating a model of a preferred embodiment of an electrochemical gas sensor network of the present invention.

FIG. 1 illustrates a model of a preferred embodiment of an electrochemical gas sensor network 24 of the present invention. The gas sensor 26 is similar to the sensor 10 as described hereinabove in conjunction with FIG. 5 and is modeled as an ideal sensor 28 and a low pass filter network 30. The transfer function of the sensor 26 in the "s" domain is the product of the transfer functions of the ideal sensor 28 and the low pass filter network 30. Because the ideal sensor 28 has a transfer function of 1 by assumption, the transfer function of the sensor 26 is the same as the transfer function of the low pass filter network 30 ($G_{cell}$).

As shown in FIG. 1, a compensation circuit 32 with a transfer function $G_{sp}$ is added to the output of the sensor 26 to amplify the high frequency component of the output signal of the sensor 26 to compensate for its attenuation. The compensated output of the circuit 32 in the s domain is expressed as:

$$\text{Signal}(s) = C_{oxygen}(s)G_{cell}(s)G_{sp}(s) \quad (8)$$

where $C_{oxygen}(s)$ is the oxygen concentration input to the sensor 26. By setting the transfer function of the circuit 32 to be the inverse transfer function of the low pass filter network 30, equation 8 becomes:

$$\text{Signal}(s) \approx C_{oxygen}(s) \quad (9)$$

It can be understood by those skilled in the art that the compensation circuit 32 can be implemented as any type of circuit suitable such as, for example, in analog technology or in digital technology as a filter.

As an example of the increase in performance of a compensated gas sensor, it can be assumed that the transfer function of the oxygen sensor $G_{cell}$ is approximated by a simple pole factor:

$$G_{cell} = 1/(1+st_1) \quad (10)$$

The 10% to 90% rise time ($R_{13}T_{10-90}$) to a step input in oxygen concentration is:

$$\text{Sensor Alone } R_{13} T_{10-90} = t_1 \times \ln 9 = 2.197 \times t_1 \quad (11)$$

For perfect compensation the desired $G_{sp}$ is:

$$G_{sp} = -A \times (1+st_1), \text{ where A is the required gain} \quad (12)$$

However, due to finite operational amplifier gain, operational amplifier bandwidth, and noise considerations, the actual $G_{sp}$ is:

$$G_{sp} = -A \times (1+st_1)/((1+st_2) \times (1+st_5)(1+st_6)), \text{ where } t_1 > t_2 >> t_5 > t_6 \quad (13)$$

Let N be defined as: $N = t_1/t_2$ then:

$$G_{cell} \times G_{sp} = (1/(1+st_1)) \times A \times ((1+st_1)/((1+st_2) \times (1+st_5)(1+st_6))) \quad (14)$$

$$G_{cell} \times G_{sp} \approx (1/(1+st_1)) \times A \times ((1+st_1)/(1+st_2)) = A/(1+st_2) = A/(1+st_1/N)) \quad (15)$$

Total System $R_{13}T_{10-90} \approx (t_1/N) \times \ln 9 = 2.197 \times t_1/N$ (16)

Thus, the rise time has been reduced by a factor of N.

For actual oxygen sensors, the transfer function is more complex than a simple pole factor. It has been determined that a primary low frequency compensation circuit transfer function ($G_{sp-lf}$) of the following form yields a reduction of the rise time and acceptably small overshoot and undershoot to a step change in the oxygen concentration:

$$G_{sp-lf} = -A \times (((1+st_1)/(1+st_2)) \times ((1+st_3)/(1+st_4))), \text{ where } t_1 > t_2 > t_3 > t_4 \quad (17)$$

The complete $G_{sp}$ has additional higher frequency poles due to finite operational amplifier gains, finite operational amplifier bandwidths, and the need to reduce high frequency noise.

Figure 2:
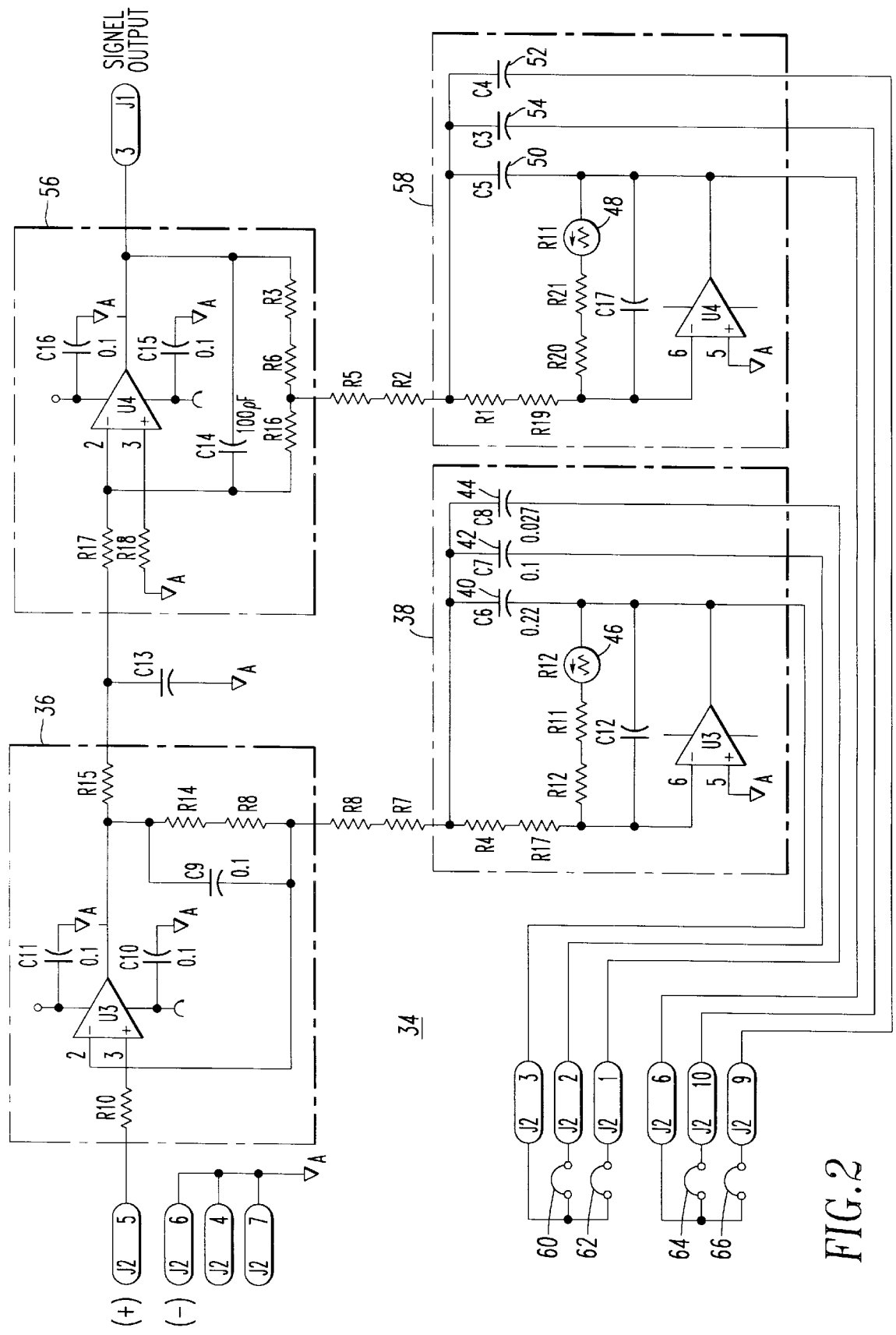
FIG. 2 is a diagram illustrating a compensation circuit.

FIG. 2 illustrates a compensation circuit 34 which is a two stage amplifier with controlled frequency response characteristics. The first stage consists of operational amplifier circuits 36 and 38. The first stage primary low frequency transfer function ($G_{sp-lf-1}$) is:

$$G_{sp-lf-1} = A_1 \times ((1+st_1)/(1+st_2)) \quad (18)$$

For the fastest sensors, the time constants $t_1$ and $t_2$ are determined by the value of capacitor 40 and the values of the associated resistors. The operational amplifier circuit 38 forms a capacitor multiplier circuit. This circuit has two advantages. First, it multiplies the effective value of the capacitor 40 (and capacitors 42 or 44, when used). This permits the use of smaller and less expensive capacitors.

Second, the operational amplifier circuit 38 causes the values of the time constants $t_1$ and $t_2$ to vary with temperature. This is necessary because the speed of response of gas sensors varies with temperature. In this particular application, the sensors speed up with increasing temperature and thermistor 46 (and 48) has a negative temperature coefficient. Thus, when the temperature increases, there is less multiplication of the value of the capacitor 40 (and 42 or 44, when used) which reduces the values of the time constants $t_1$ and $t_2$. This reduces the amount of high frequency sensor signal amplification, which matches the reduced need for high frequency sensor signal amplification. This, combined with the similar temperature correction of the compensation in the second stage, results in a total system (sensor and compensation circuit) speed of response which is approximately independent of temperature changes. For sensors which slow down with increasing temperature a positive temperature coefficient thermistor could be used for the thermistor 46 (and 48) to result in increasing values for the time constants $t_1$ and $t_2$ with increasing temperature. Note that because two capacitor multiplier circuits are used, the temperature coefficient of the time constants $t_1$ and $t_2$ can be different in magnitude and/or polarity from the temperature coefficient of the time constants $t_3$ and $t_4$.

There is a spread in the speed of response of oxygen sensors for which a correction needs to be made to maintain acceptable total system performance. This correction is accomplished by using the capacitor 40 alone for sensors in the range of the fastest speed of responses, or the capacitor 44 in parallel with the capacitor 40 for the sensors in the range of the medium speed of responses, or the capacitor 42 in parallel with the capacitor 40 for the sensors in the range of the slowest speed of responses. Thus the amount of compensation provided is matched with the compensation needed by the sensors. A similar correction is made in the second stage using capacitors 50, 52 and 54.

After a sensor eletrochemical cell is produced, its required compensation is determined and, as shown in FIG. 2, jumpers 60, 62, 64, and 66 are placed (or not placed) on that sensor's printed circuit board (PCB). These jumpers on the sensor PCB control which (if any) capacitors are placed in parallel with the capacitor 40 (and the capacitor 50) on the compensation circuit 34. Thus, when an oxygen sensor is replaced, the jumpers on the new sensor PCB determine the correct compensation to be made by the compensation circuit without operator intervention.

The second stage consists of operational amplifier circuits 56 and 58. The second stage primary low frequency transfer function ($G_{sp-lf-2}$) is:

$$G_{sp-lf-2} = -A_2 \times ((1+st_3)/(1+st_4)), \text{ where } A_2 = A/A_1 \quad (19)$$

The operation of the second stage is similar to that of the first stage except that it inverts the polarity of the signal.

It can be understood by those skilled in the art that more stages could be used in the compensation circuit to yield a total transfer function with more terms which could more closely match the inverse of the oxygen sensor's transfer function. For a step change in oxygen concentration, this could further reduce the total system rise time ($R\_T_{10-90}$) and could reduce the overshoot and undershoot of the output signal.

After sensor electrochemical cells are produced, the magnitude of their direct current outputs for a given target gas concentration can be measured. The cells are sorted into several different ranges of output current. The cells of a given range are connected to a sensor PCB with resistor values for the resistors across the sensor output that yield a sensor output signal within a given smaller range of magnitudes. All of the sensor output signals would have the same range of output voltage magnitudes and this range would have a smaller percentage spread than the percentage spread of all the electrochemical cell output currents. Thus, all of the sensor output voltages would be normalized to an acceptably small range and sensors could be replaced without operator intervention for the magnitude of the basic electrochemical cell output current.

A temperature compensation circuit can also be placed between the sensor output and the compensation circuit 34 to compensate for the change in the DC gain of the sensor that occurs with a change in temperature.

A filter may be added to the output of the compensation circuit to eliminate chopper noise and any environmental power source frequency noise that may be picked up from the power source.

Figure 3:
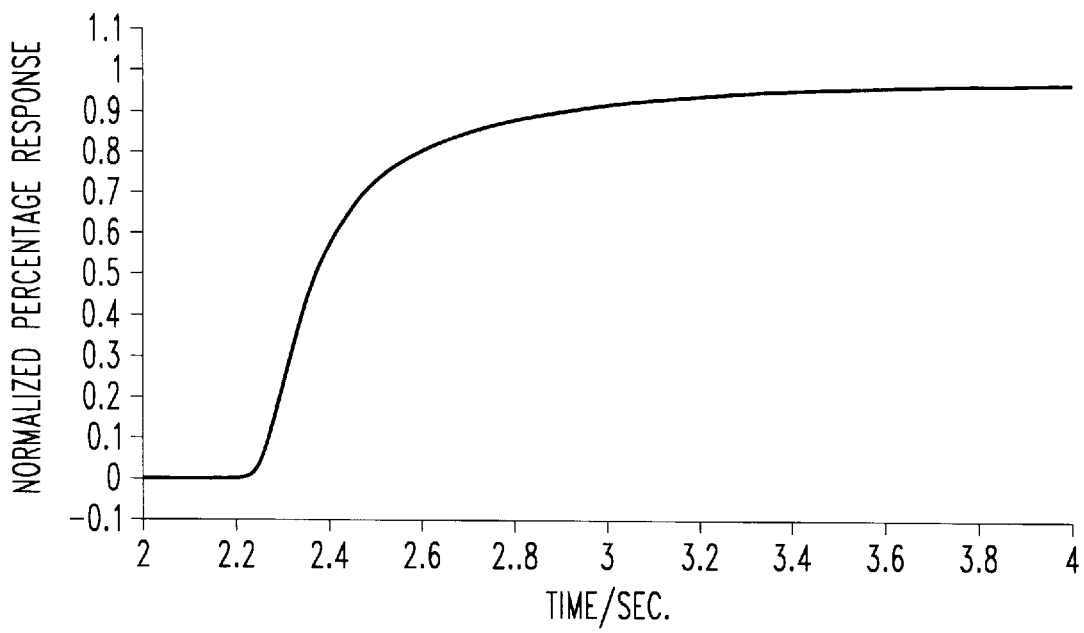
FIG. 3 illustrates a typical output of a Teledyne Analytical Instruments Model R-24* sensor in response to a step change oxygen input.
Figure 4:
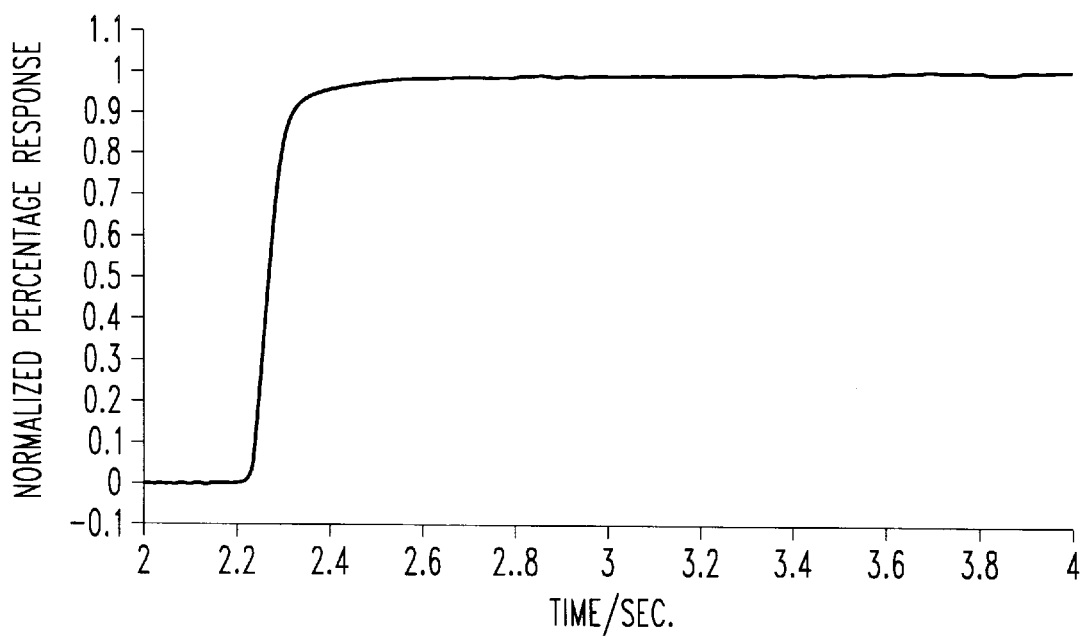
FIG. 4 illustrates the output of the compensation circuit when connected to an R-24* sensor with a step change oxygen input to the sensor.

FIG. 3 illustrates a typical output of a Teledyne Analytical Instruments Model R-24* sensor in response to a step change oxygen input. The response curve was measured at room temperature, from 21% to 100% oxygen at a flow rate of 100 ml/min. FIG. 4 illustrates the output of the circuit 34 when connected to an R-24* sensor with a step change oxygen input to the sensor. The response curve was measured at room temperature, from 21% to 100% oxygen at a flow rate of 100 ml/min.

While the present invention has been described in conjunction with preferred embodiments thereof, many modifications and variations will be apparent to those of ordinary skill in the art. For example, the transfer function of the compensation circuit can be implemented using digital filtering techniques by digitizing the sensor output and then processing the digital signal using digital filter techniques such as, for example, finite impulse response (FIR) or infinite impulse response (IIR). FIG. 1A is a diagram illustrating such an embodiment. The network 24 includes a digital filter 33, which may be, for example, a finite impulse response (FIR) or infinite impulse response (IIR) filter. The foregoing description and the following claims are intended to cover all such modifications and variations.

What is claimed is:

1. A gas sensor network, comprising:
   a gas sensor for receiving a gas and for generating a target gas concentration signal, the gas sensor having an output terminal for providing an output signal that is a product of said target gas concentration signal and a first transfer function; and
   a frequency compensation circuit having an input terminal connected to said output terminal of said gas sensor, and having an output terminal providing an output signal that is a product of said output signal from said gas sensor and a second transfer function, said second transfer function being approximately an inverse of said first transfer function.

2. The network of claim 1, wherein said frequency compensation circuit includes a temperature compensation circuit.

3. The network of claim 1, wherein said second transfer function is a quotient of a first number of factors and a second number of factors.

4. The network of claim 3, wherein said first number is less than said second number.

5. The network of claim 4, wherein said second transfer function is one transfer function divided by a product of two transfer functions.

6. The network of claim 3, wherein said first number is equal to said second number.

7. The network of claim 1, wherein said frequency compensation circuit includes an operational amplifier circuit.

8. The network of claim 7 wherein said operational amplifier circuit includes a two stage amplifier circuit and a temperature compensation circuit.

9. The network of claim 8 wherein said frequency compensation circuit further includes a temperature measuring device.

10. The network of claim 1 wherein said frequency compensation circuit includes a digital filter.

11. The network of claim 10 wherein said digital filter includes an FIR filter.

12. The network of claim 10 wherein said digital filter includes an IIR filter.

13. An electrochemical gas sensor network, comprising:
    means for sensing a gas, said means producing an output signal that is a product of a target gas concentration signal and a first transfer function; and
    means, connected to said means for sensing, for amplifying a high frequency component of said output signal of said means for sensing, said means for amplifying having an output signal that is a product of said output signal of said means for sensing and a second transfer function being approximately an inverse of said first transfer function.

14. An electrochemical gas sensor network, comprising:
    means for sensing a gas, said means producing an output signal that is a product of a target gas concentration signal and a first transfer function; and
    means, connected to said means for sensing, for digitally compensating for an attenuated high frequency component of said output signal of said means for sensing a gas, said means for digitally compensating providing an output signal that is a product of said output signal of said means for sensing a gas and a second transfer function being approximately an inverse of said first transfer function.

15. A method of compensating for the attenuation of a high frequency component of an output signal of a gas sensor, the output signal being a product of a target gas concentration signal and a first transfer function, comprising the step of amplifying a high frequency component of said output signal with a circuit providing an output signal that is a product of the output signal of the gas sensor and a second transfer function being approximately an inverse of the first transfer function.

16. The method of claim 15 wherein said step of amplifying a high frequency component of said output signal includes the step of compensating said output signal of said circuit for temperature changes in said gas sensor.

17. A method of compensating for the attenuation of a high frequency component of an output signal of a gas sensor, the gas sensor having an output signal that is a product of a target gas concentration signal and a first transfer function, comprising the steps of:
    digitizing the high frequency component of the output signal; and
    filtering said digitized signal with a circuit having an output signal that is a product of the output signal of the gas sensor and a second transfer function being approximately an inverse of the first transfer function.

* * * * *